United States Patent
Albuquerque et al.

(10) Patent No.: US 9,983,187 B2
(45) Date of Patent: May 29, 2018

(54) METHOD FOR EXTRACTING PRECURSOR ACIDS FROM CALCIUM NAPHTHENATE DEPOSITS

(71) Applicant: PETROLEO BRASILEIRO S.A.—PETROBRAS, Rio de Janeiro, RJ (BR)

(72) Inventors: Flávio Cortiñas Albuquerque, Petropolis (BR); Rafael dos Santos Nascimento de Brito, Rio de Janeiro (BR); Marcele Abreu Lopes, Rio de Janeiro (BR)

(73) Assignee: PETROLEO BRASILEIRO S.A.-PETROBRAS, Rio de Janeiro (BR)

( * ) Notice: Subject to any disclaimer, the term of this patent is extended or adjusted under 35 U.S.C. 154(b) by 213 days.

(21) Appl. No.: 14/861,364

(22) Filed: Sep. 22, 2015

(65) Prior Publication Data

US 2016/0153956 A1 Jun. 2, 2016

(30) Foreign Application Priority Data

Nov. 28, 2014 (BR) .......................... 10 2014 029770

(51) Int. Cl.
G01N 33/00 (2006.01)
G01N 33/28 (2006.01)
C10G 25/00 (2006.01)

(52) U.S. Cl.
CPC ......... *G01N 33/2835* (2013.01); *C10G 25/00* (2013.01); *C10G 2300/1037* (2013.01); *C10G 2300/203* (2013.01); *C10G 2300/80* (2013.01)

(58) Field of Classification Search
CPC .................................................. G01N 33/2835
USPC ............................................................ 422/68
See application file for complete search history.

(56) References Cited

U.S. PATENT DOCUMENTS

| 4,070,271 A * | 1/1978 | Carlson ................. C10G 53/14 208/206 |
| 8,674,161 B2 | 3/2014 | Mediaas et al. |
| 2012/0116138 A1* | 5/2012 | Goodall ................. C10G 45/08 585/357 |

FOREIGN PATENT DOCUMENTS

| CN | 103320160 A | 9/2013 |
| CN | 103805227 A | 5/2014 |

OTHER PUBLICATIONS

Janson (Protein Purification: Principles, High-Resolution Methods, and Applications, 1998).*
Qilie Luo and Joseph D. Andrade "Cooperative Adsorption of Proteins onto Hydroxyapatite" Journal of Colloid and Interface Science 200, 104-113 (1998).*

* cited by examiner

*Primary Examiner* — Christine T Mui
*Assistant Examiner* — Emily R. Berkeley
(74) *Attorney, Agent, or Firm* — Sughrue Mion, PLLC

(57) ABSTRACT

The present invention is a system for the extraction and quantification of tetraprotic naphthenic acids present in oils, precursors of the formation of calcium naphthenates, which are potential formers of deposits, causing of damage to pieces of equipment used in the oil production industry.

8 Claims, No Drawings

METHOD FOR EXTRACTING PRECURSOR ACIDS FROM CALCIUM NAPHTHENATE DEPOSITS

FIELD OF THE INVENTION

The present invention falls within the field of oil production processes, making it possible to quickly make the prognosis in laboratory scale of the deposition of calcium naphthenates in order to prevent the deposition of these compounds, which would impact the production and profitability of oil production units.

BASIS OF THE INVENTION

High oil prices made it economically feasible to produce lower-quality crudes, namely, those of lower API grade, between 10 and 20, which are the more acidic oils, between 1 and 10 mg KOH/g, and those which are produced in the most adverse conditions: offshore, in deep and ultra-deep waters, between 1,000 and 3,000 m water depth.

Due to higher costs for drilling and cementing offshore wells, only high productivity projects, in excess of 10,000 barrels of oil per day (bpd), are deemed attractive. The achievement of these goals can be threatened by the deposition of calcium naphthenates. Unlike the fouling of inorganic salts, such as strontium sulfate, barium sulfate, and calcium carbonate, which can be foreseen and even managed, the formation of calcium naphthenate deposits cannot be predicted with a safety margin.

The formation of calcium naphthenate deposits occurs due to the gradual oil decompression from reservoir conditions to surface conditions, when carbon dioxide evolves to its gas phase, causing the elevation of the pH in the produced water. The increase in pH makes the naphthenic acids (carboxylic acids found in the oil) migrate to the water/oil interface and interact with cations found in the produced water. Certain tetraprotic carboxylic acids, if present in oil, can react with calcium ions to form a calcium naphthenate interfacial film, which accumulates and is deposited inside of separators, blocks valves, and clogs filters and heat exchangers. In a few months, the accumulated amount of salt deposits can reach a few tons, making it impossible for the unit to continue operational.

The increased produced water pH, the presence of calcium ions and tetraprotic acids in oil cannot, in principle, be controlled; only at an exorbitant cost. It is hard to determine the content of tetraprotic acid in oil alone, because they are usually present in very low levels. However, even with all this knowledge, it is not possible to predict the deposition of calcium naphthenate salts, given the possible existence of natural calcium naphthenate inhibitor substances in the oil. Those substances act as surfactants and compete for the water/oil interface slowing or preventing the reaction of tetraprotic acids with calcium.

The unpredicted deposition of calcium naphthenate impacts on the profitability of offshore oil production facilities, considering that oil production must be halted for several days for cleaning, unclogging, and descaling of the equipment, a difficult and time-consuming process. The cost of stopping an offshore oil production unit could reach tens of millions of dollars a day. The removed deposits have to be transported since they can only can be properly disposed of on land, an obviously expensive operation. There are commercial chemicals that inhibit deposition of calcium naphthenate, but the prediction of optimal injection points, and the chemical itself, have an impact on the fixed cost of the oil production system.

Currently, it is only possible to assess the risk of the deposition of calcium naphthenate in oil production, in equipments, or to evaluate the performance of chemicals that inhibit this deposition, with the use of physical simulators which require large volumes of oil samples, in the order of tens of liters. Such sample volumes are typically available only for long-term tests during the oil production, at a time when it is still not clear whether there will be calcium naphthenate deposition of in the future. Additionally, physical simulators have limited capacity to test many samples in a given period of time (1 sample/day).

In Patent document CN103805227(A) Liu Jianchun et al. details a pre-treatment process for high acidity crude oils. The process comprises deacidification, by chemical extraction, and coupled electrostatic desalting. In this case, the naphthenate is extracted in solvent phase and then acidified for the separation of the naphthenic acid.

In Patent document CN103320160(A) Yang Zhe et al details an acidity and salt reduction process for crude oils by means of aquathermolysis and desalting. In aquathermolysis 85% of the acid content in the crude oil are removed. The naphthenates present during the desalting process act as emulsifiers, increasing the efficiency of the process up to 90%.

American patent U.S. Pat. No. 8,674,161 B2 describes a method for isolation and quantification of naphthenic acids formation in crude oils. The method involves the selective absorption/adsorption of naphthenic acids in solid medium. The absorbed/adsorbed naphthenic acids are extracted from the solid medium by means of an organic solvent and the naphthenic acid content is analyzed.

SUMMARY OF THE INVENTION

The invention consists of a laboratory system and test method, which can help determine if there is a calcium naphthenate deposition risk associated with a particular oil, and classify that risk.

DESCRIPTION OF THE INVENTION

The calcium naphthenate deposition risk is established by the formation of calcium naphthenate on the interface between the oil sample tested, a sample which can be diluted in organic solvent, and an aqueous solution of calcium ions with buffered pH. The calcium ion concentration and the pH value of the aqueous solution are defined in order to make it possible for the tetraprotic naphthenic acids, eventually present in the sample, to react and form a calcium naphthenate film on the interface between the aqueous/oily phases. After the separation of the hydrocarbons and other components of the oil sample, the substances retained on the water/oil interface are extracted by contact with solutions containing adequate acid and organic solvents.

Any acids that do not form insoluble calcium salts or complexes and which have a constant ionization greater than $1.0 \times 10^{-5}$, such as hydrochloric, hydrobromic, nitric, acetic, formic, propionic or butyric acid, in concentrations between $1.0 \times 10^{-4}$ mol/L and 12 mol/L are adequate.

Solvents which are immiscible with water, with a normal boiling point below 110° C., and able to dissolve tetraprotic naphthenic acids, such as dichloromethane, chloroform or toluene, either pure or mixed with methanol, ethanol or isopropanol are adequate.

The deposition, or its absence, of calcium naphthenate on the water/oil interface is predicted by the quantification of tetraprotic naphthenic acids present in the residue of solvent evaporation from the organic extract.

The system where the formation of calcium naphthenate occurs is designed in such a way as to maximize the interface between the oily oil sample and the buffered solution containing calcium ions, besides making the purification and isolation of the substances retained on the water/oil interface possible. The system and test method require only a few tens of grams of oil sample, being therefore compatible with the available sample scale in formation tests. Since this test is more easily performed, it can be applied to a larger number of samples when compared to tests performed in a physical simulator.

By pointing the risk of calcium naphthenate deposition well in advance, the method makes it possible to indicate the need for injection points and the amount of chemicals to inhibit calcium naphthenate deposition from the time the production unit is designed, as well as to determine associated costs. Depending on the degree of safety demanded by the project, the invention can be used as a filter, a critical point, to determine which oils need to be evaluated in a physical simulator.

The invention is also applicable to the preliminary performance evaluation of calcium naphthenate deposition inhibitor chemicals.

The quantification of tetraprotic naphthenic acids in the oil indicates that those acids are prone to react and to form calcium naphthenate on a water/oil interface, representing risk of deposition. In an equivalent manner, the absence of tetraprotic acids in the oil indicates that those substances are not present in the sample or the sample contains surfactants slowing or preventing the substance to reach the water/oil interface and, as a consequence, slowing or inhibiting calcium naphthenate deposition. The performance of the calcium naphthenate deposition inhibitors, which act in the same way as the natural surfactants, is investigated through this system and test method, since both explore the same inhibition mechanism.

Example 1

The extraction system consists of a glass column with a sintered glass plate and flow control bottom tap, a feeding funnel on top of the glass column and a Kitasato flask at the glass column outlet. Granular solids are placed inside the column, such as diatomaceous earth, 10 to 15 Gr, with adequate granulometry, i.e. an average particle diameter above 0.1 mm; to the gravitational percolation of liquids, such as a buffered aqueous solution of calcium or an oil sample. The solid must have preferential affinity for aqueous solutions and high capacity for absorbing liquids. Glass beads are placed over the bed of solids, in sufficient quantity to prevent the dripping of liquids from the feeding funnel from revolving the bed.

50 ml of an aqueous solution of calcium ions 0.5 mol/L with buffered pH, typically between 7.0 and 8.0, are introduced in the column packed with diatomaceous earth. The buffering agent must be compatible with the calcium ions in the buffer, such as tris(hydroxymethyl)aminomethane (TRIS) in a concentration of 0.1 mol/L. After the full volume of the buffered calcium solution has covered the absorbing bed, the column tap is closed and it is necessary to wait a few minutes, between 5 and 30 min, for the maximum absorption of the buffer to occur. The part of the solution which was not absorbed is removed from the column by opening the tap and draining the system into a Kitasato flask. Then, the addition of the oil sample begins, typically a volume between 10 and 100 Gr, through the feeding funnel. In general, it is necessary to dilute the oil sample with a low polarity solvent, typically toluene, to reduce the viscosity and increase the diffusivity of components with interfacial affinity. In general, the ratio of oil sample/solvent used is in a range between 1:1 and 1:2. Liquid flow through the bed is adjusted with the column tap so it flows slowly, around 1 drop every 3 s.

When the oil sample and solvent mixture finish passing, an additional volume of solvent is percolated, equivalent to 15-20 times the mass of solids used on the bed, typically the volume of additional solvent used is within a range of 100-250 ml, with the goal of removing from the column the hydrocarbons present in the oil sample and other substances which are not present in the water/oil interface. The solvents used in this step are toluene or dichloromethane.

The desorption of interface components and, eventually, the regeneration of tetraprotic naphthenic acids, is promoted by the action of an acid, such as hydrochloric or formic acid, in sufficient quantity to acidify the solution of calcium ions. To this end, it is appropriate the percolation by the bed of 50 ml of hydrochloric acid at 1.0 mol/L, or 50 ml of solution at 10% (v/v) of formic acid in dichloromethane.

In case hydrochloric acid solution in a concentration of 1.0 mol/L is used, this solution is collected along with the organic solvents adequate for dissolving tetraprotic naphthenic acids, such as dichloromethane, chloroform or toluene, pure or in mixtures containing up to 30% of methanol or ethanol, after percolation by the bed. Volumes equivalent to 4-6 times the mass of granular solids that make up the bed of dichloromethane, and the mixture of dichloromethane and methanol (at a 95:5 ratio), typically 50 ml of dichloromethane and 50 ml of dichloromethane and methanol mixture (95:5 ratio), are percolated.

The aqueous and organic phases are subsequently separated in a decanting funnel, and the organic phase is set aside. In case the dichloromethane and formic acid mixture at 10% (v/v) is chosen, only the percolation of the dichloromethane and methanol mixture (95:5 ratio) is required (volume equal to 4-6× the mass of the bed, or typically 50 ml), and this is collected together with the first.

In both cases, organic solvents are evaporated in a rotary evaporator or under a nitrogen jet until a constant weight of the residue is achieved, which must consist of oil substances with affinity for the water/oil interface, with the calcium ion buffered solution, eventually including tetraprotic naphthenic acids.

The research for tetraprotic naphthenic acids in the evaporation residue is made using analytical techniques suitable for this purpose, such as high-performance liquid chromatography (HPLC) or ultra-high resolution mass spectrometry (FT-ICR-MS). The method of Simon et al. was found to be appropriate (Journal of Chromatography A, v., 1200 n. 2, p. 136-143, 2008, Determination of C80 tetraacid content in calcium naphthenate deposits), which has the additional advantage of allowing the quantification of tetraprotic naphthenic acids.

Example 2

Three 100 ml fractions of tetraprotic naphthenic acids solution in a concentration of 10 mg/l in toluene were extracted in three essays with 12 g of diatomaceous earth soaked in an buffered aqueous calcium chloride solution at 0.5 mol/L, using the system for risk assessment of calcium naphthenate deposition. In each of the extractions, the pH was buffered in 6.3, 8.0 and 9.0, respectively with bis(2-hydroxyethyl)amino-tris(hydroxymethyl)methane (BIS-TRIS) and TRIS. The other conditions of the test method were maintained.

The presence of tetraprotic naphthenic acids in their respective extract evaporation residues was detected using the high-performance liquid chromatography technique, in analysis conditions based on Simon et al. (2008), after derivatization with 2-bromo-2-acetonaphthone. The chromatograms show that the recovery of tetraprotic acids in the evaporation residue is increasing, reaching a recovery of tetraprotic acid close to 100% at pH 9.0, as presented in Table 1. There were no natural inhibitors of calcium naphthenate deposition in the tetraprotic acids solution in toluene.

TABLE 1

| Buffer used (concentration in mol/L) | pH of the $CaCl_2$ aqueous solution at 0.5 mol/l | % recovery of tetraprotic acids |
|---|---|---|
| BIS-TRIS 0.1 | 6.3 | 1.1 |
| TRIS 0.1 | 8.0 | 7.3 |
| TRIS 0.1 | 9.0 | 103 |

Example 3

Three fractions equivalent to 50 g each of oil known to lead to calcium naphthenate deposition were diluted in 100 ml of toluene, and extracted, each fraction with 12 g of diatomaceous earth soaked in an buffered solution of calcium chloride at 0.5 mol/L, using the system for risk assessment of calcium naphthenate deposition. In each of the extractions, the pH was buffered in 7.0, 8.0 and 9.0, with BIS-TRIS and TRIS respectively. The other conditions of the test method were maintained. The presence of tetraprotic naphthenic acids in their respective extract evaporation residues was detected using the high-performance liquid chromatography technique, in analysis conditions based on Simon et al. (2008), after derivatization with 2-bromo-2-acetonaphthone. Results indicate a maximum content of tetraprotic acids in oil when the solution of calcium chloride at 0.5 mol/L with pH 8.0 was used, as shown in TABLE 2. It indicates that is, among the pH adjusted values, the one in which the calcium naphthenate deposition occurs at maximum. Note that tetraprotic acids were not detected in the evaporation residue when a calcium chloride solution buffered in pH 9.0 was used. Although the recovery of tetraprotic acids observed in Example 2 was the maximum in this pH, competition for the aqueous solution interface with oil exerted by natural inhibitors prevented or slowed the calcium naphthenate deposition of calcium in the system.

TABLE 2

| Buffer used (concentration in mol/L) | pH of the $CaCl_2$ aqueous solution at 0.5 mol/l | Tetraprotic acids content in the sample (mg/kg) |
|---|---|---|
| BIS-TRIS 0.1 | 7.0 | 1.7 |
| TRIS 0.1 | 8.0 | 5.6 |
| TRIS 0.1 | 9.0 | Not detected |

Example 4

Five fractions equivalent to 50 g each of oil known to lead to the deposition of calcium naphthenate were diluted in 100 ml of toluene and extracted, each fraction with 12 g of diatomaceous earth soaked in an aqueous solution of calcium chloride at 0.5 mol/L, buffered at pH 8.0 with TRIS at 0.1 mol/L. Again, the presence of tetraprotic naphthenic acids in their respective extract evaporation residues was detected using the high-performance liquid chromatography technique, in analysis conditions based on Simon et al. (2008), after derivatization with 2-bromo-2-acetonaphthone. The results indicate the reproducibility of the system for assessment of calcium naphthenate deposition risk and the test method, as shown in TABLE 3.

TABLE 3

| Determination | Tetraprotic acids content in the sample (mg/kg) |
|---|---|
| 1 | 3.6 |
| 2 | 3.8 |
| 3 | 6.5 |
| 4 | 2.8 |
| 5 | 3.2 |

Example 5

Two fractions equivalent to 50 g each of an oil of which the production unit does not present calcium naphthenate deposition, were diluted with 100 ml of toluene (non-doped sample) and with 100 ml of toluene containing tetraprotic naphthenic acids at 10 mg/l (doped sample). Both fractions were extracted with 12 g of diatomaceous earth soaked in an aqueous solution of calcium chloride at 0.5 mol/L, buffered at pH 8.0 with TRIS at 0.1 mol/L. The presence of tetraprotic naphthenic acids in their respective extract evaporation residues was evaluated using the high-performance liquid chromatography technique, in analysis conditions based on Simon et al. (2008), after derivatization with 2-bromo-2-acetonaphthone. Results show analyses of the non-doped and doped samples, and of a tetraprotic naphthenic acids solution at 15 mg/l. Analysis of the doped and non-doped oil samples show no signs of tetraprotic acid-related peaks. Besides, they are indistinguishable and indicate the existence of natural inhibitors of calcium naphthenate deposition in that oil, which therefore does not present any risk of deposition.

The invention claimed is:

1. A method for extracting precursor acids from calcium naphthenate deposits comprising the following steps:
    filling a glass column with granulated solids with affinity for aqueous solutions;
    adding a buffered calcium ion aqueous solution to the glass column;
    waiting for a predetermined period of time for maximum absorption of the buffered calcium ion aqueous solution by the granulated solids;
    removing a non-absorbed portion of the buffered calcium ion aqueous solution, draining said portion into a Kitasato flask;
    adding an oil sample to be tested to the glass column;
    adjusting the flow of a percolated liquid in the glass column to 1 drop every 3 seconds;
    percolating an additional volume of a solvent equivalent to 15-20 times the mass of the granulated solids used in the glass column;
    percolating an acid solution in order to desorb components present in the oil retained on a water/oil interface;

percolating dichloromethane and then a methanol solution in dichloromethane at 5% v/v;

separating an aqueous phase and an organic phase in a separation funnel;

setting aside the organic phase;

evaporating the solvent from the organic phase in a rotary evaporator until a constant residue mass achieved; and analyzing and quantifying tetraprotic naphthenic acids in the evaporation residue.

2. The method according to claim 1, wherein the granulated solids are diatomaceous earth.

3. The method according to claim 2, wherein the granulated solids are chemically inert and wettable by water, and presenting a granulometry above 0.1 mm.

4. The method according to claim 1, wherein the calcium ion aqueous solution is in a concentration range from 0.01-1 mol/L and buffered with tris(hydroxymethyl)aminomethane (TRIS) and/or bis(2-hydroxyethyl)amino-tris(hydroxymethyl)methane (BIS-TRIS).

5. The method according to claim 1, wherein the oil sample is diluted in toluene containing tetraprotic naphthalene acids in a concentration of 0-10 mg/l prior to being added to the glass column.

6. The method according to claim 1, wherein the percolation with the additional volume of the solvent is performed with toluene and/or dichloromethane.

7. The method according to claim 1, wherein the acid solution is hydrochloric acid in a concentration of 1.0 mol/L or formic acid in dichloromethane solution at 10% (v/v).

8. The method according to claim 1, wherein the predetermined period of time is between 5 and 30 minutes.

* * * * *